United States Patent [19]
Satake et al.

[11] Patent Number: 5,434,119
[45] Date of Patent: Jul. 18, 1995

[54] TRANSPARENT RECORDING MEDIUM

[75] Inventors: Toshimi Satake; Tomoaki Nagai; Toshiyuki Takano; Akio Sekine, all of Tokyo, Japan

[73] Assignee: Jujo Paper Co., Ltd., Tokyo, Japan

[21] Appl. No.: 903,566

[22] Filed: Jun. 24, 1992

[30] Foreign Application Priority Data

Jun. 24, 1991 [JP] Japan .................. 3-151311

[51] Int. Cl.$^6$ ............ B41M 5/30; B41M 5/40
[52] U.S. Cl. ................. 503/216; 427/150; 430/200; 430/201; 430/202; 430/945; 503/225
[58] Field of Search ......... 427/10; 503/216, 225; 430/200, 201, 945

[56] References Cited

FOREIGN PATENT DOCUMENTS

| | | | |
|---|---|---|---|
| 2526716 | 11/1983 | France | 503/216 |
| 58-94494 | 6/1983 | Japan | 503/216 |
| 58-209594 | 12/1983 | Japan | 503/216 |
| 59-2880 | 1/1984 | Japan | 503/216 |
| 0032697 | 2/1985 | Japan | 503/216 |
| 60-184879 | 9/1985 | Japan | 503/216 |
| 60-210491 | 10/1985 | Japan | 503/216 |
| 63-45087 | 2/1988 | Japan | 503/216 |
| 63-137888 | 6/1988 | Japan | 503/216 |
| 1-294088 | 11/1989 | Japan | 503/216 |
| 659975 | 3/1987 | Switzerland | 503/216 |
| 2112160 | 7/1983 | United Kingdom | 503/209 |

*Primary Examiner*—B. Hamilton Hess
*Attorney, Agent, or Firm*—Burgess, Ryan & Wayne

[57] ABSTRACT

A transparent recording medium is disclosed which can directly record a fine, precise image. With the recording medium, a compact, fine image occupying a small storage space can be easily enlarged and confirmed by an enlarged projection. It is prepared by applying a coating liquid for recording comprising a developer in which a hydroxyl group with a developing function is blocked by an N-substituted carbamoyl group or an O-substituted oxycarbonyl group, an iron salt of an organic acid or a leuco dye, a near-infrared absorbing agent, and a binder, uniformly dissolved in an organic solvent such as MEK, to a transparent plastic substrate, and drying to obtain a transparent recording layer with a thickness of 3 μm to 8 μm. A visible, precise, fine direct image can then be recorded using a semiconductor laser beam.

20 Claims, No Drawings

TRANSPARENT RECORDING MEDIUM

BACKGROUND OF THE INVENTION

1. Field of the Invention

The present invention relates to a transparent recording medium providing recording with absorption in the visible range directly by heat or light.

2. Description of the Background Art

Conventionally, the following recording media are known for obtaining recording with absorption in the visible range directly by heat or light.

For a heat-sensitive recording medium used with a facsimile machine or the like, a colorless or light-colored electron donor dye (leuco dye) and a developer are dispersed and mixed in an aqueous solution of a water-soluble binder, and pulverized into minute particles to obtain a painting liquid. The painting liquid is applied to a nontransparent support member such as paper.

Japanese Patent Laid-open (ko-kai) Nos. 294088/1989 and 45087/1988 disclose a transparent heat sensitive recording medium prepared by dissolving a dye and a developer in an organic solvent and by applying to a transparent medium, wherein a nitrogen- or sulfur-containing onium compound is used as both a developer and thermal activation agent.

These are materials for recording the image by the direct heating method in which a thermal head is brought into contact with a recording medium and the medium is directly heated.

On the other hand, media and methods for recording an image by irradiating near-infrared light without direct heating are disclosed in Japanese Patent Laid-open (ko-kai) Nos. 94494/1983, 2880/1984, and 42994/1983. Japanese Patent Laid-open (ko-kai) No. 94494/1983 discloses an optical recording medium prepared by applying a coating liquid comprising a near-infrared absorbing agent dispersed in a water soluble binder, in addition to a leuco dye and a developer, to a support member. Japanese Patent Laid-open (ko-kai) Nos. 2880/1984 and 42994/1983 disclose optical recording media prepared by individually laminating a dye, a developer, and a near-infrared absorbing agent on a substrate by vacuum evaporation. Also, Japanese Patent Laid-open (ko-kai) No. 209594/1983 discloses a heat-sensitive recording medium wherein background fogging is prevented by the provision of an isolation layer prepared by coating a near-infrared absorbing agent in the interface of a coating layer, prepared by applying a solution of a color developer, e.g., a leuco dye, in an organic solvent to a substrate, and a layer of a developer solution provided on the coating layer.

However, the recording layer of a normal heat-sensitive recording medium comprising an electron donor colorless dye and a developer is opaque, because such a layer uses a dispersed coating liquid prepared by adding a developer and a dye reduced to minute particles in an aqueous medium, together with an auxiliary or filler. Such a recording medium therefore cannot function as a transparent recording medium. If a dye and a developer are simply dissolved in an organic solvent, the dye and the developer react with each other and develop a color so that such a composition cannot be used as a recording medium coating liquid.

On the other hand, in a composition in which an onium compound, as a developer, and a dye are dissolved together in an organic solvent, the onium salt does not react with the dye and no color is developed under normal conditions. Therefore, the composition can be used as a transparent heat-sensitive recording medium coating liquid. However, the decomposition reaction of the onium salt by the thermal energy is rather slow; no quick and adequate decomposition reaction is initiated by a thermal lead or by thermal energy produced by a light-heat conversion process by a semiconductor laser. Thus, it is essentially impossible to obtain a practical recording material with good sensitivity from such a composition. Furthermore, safety of the material is a problem, since an onium salt must be bonded to antimony hexafluoride, phosphorus hexafluoride, arsenic hexafluoride, or the like, as a counter anion.

The composition prepared by dispersing a dye, a developer and a near-infrared absorbing agent together with a binder is nontransparent. Therefore, such a composition cannot be used as a recording layer of a transparent recording medium. The method respectively laminating a dye, a developer, and a near-infrared absorbing agent by vacuum evaporation onto a substrate is unsuitable as a method for obtaining a normal transparent recording member from the aspect of transparency of the recording layers and cost.

High cost and incapability of mass production are problems in the transparent heat-sensitive recording medium in which an isolation layer of a near-infrared absorbing agent is provided between a dye layer and a developer layer, on account of the requirement of providing at least three layers. Another problem in this type of recording medium is contamination of components in one layer into other layers when coating is carried out, because colores are developed between the layers by the contamination.

Accordingly, the object of the present invention is to provide, with due consideration to the drawbacks of such conventional transparent recording media, a transparent recording medium on which a precise recording with an absorption in the visible range can be obtained directly by means of light or heat, using a coating composition comprising all necessary materials completely dissolved in a single solution.

SUMMARY OF THE INVENTION

This object is achieved according to the present invention by the provision of a transparent recording medium comprising a transparent supporting medium and a transparent recording layer formed on said transparent supporting medium, wherein said transparent recording layer comprises:

a developer formed by blocking at least one hydroxyl group with a developing function by an N-substituted carbamoyl group (—C(=O)NH—R$_1$) or O-substituted oxycarbonyl group (—(C=O)OR$_2$), which developer is represented by the following formula (1),

(wherein R is a substituted or unsubstituted aryl group, R$_A$ is a group

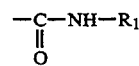

or a group

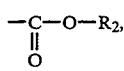

wherein $R_1$ and $R_2$ individually represent a substituted or unsubstituted alkyl group, cycloalkyl group, vinyl group, allyl group, aryl group, benzyl group, naphthyl group, mesyl group, or tosyl group, $R_1$ and $R_2$ may be the same or different when n is 2 or more; n and m are integers of 1–3, provided that $m \leq n$), and a metal salt of an organic acid or a leuco dye which develops a color by reacting with said developer.

Among developers represented by formula (1), compounds represented by the following formulas (2) or (3) are more preferable.

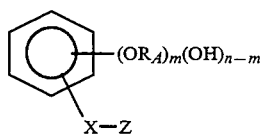

(2)

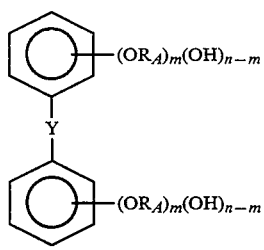

(3)

(wherein $R_A$, n and m have the same meanings as defined for formula (1); X represents COO, CONH, or $SO_2$; Z is an alkyl group, an alkoxyphenyl group, or a benzyl group; and Y is $C(CH_3)_2$, $CHR_B$, $CH((C=O)OR_B)$, S, $SO_2$, S—$R_C$—S, O—$R_C$—O, (C=O)O—$R_C$—O(C=O), or S—$R_C$—O—$R_C$—O—$R_C$—S, wherein $R_B$ is an alkyl group or an aryl group; and $R_C$ is an alkylene group).

A transparent optical recording medium with good sensitivity can be obtained by solubilizing and incorporating a light absorbing agent capable of converting absorbed light into heat in the transparent recording layer.

Other and further objects, features and advantages of the present invention will appear more fully from the following description.

DETAILED DESCRIPTION OF THE INVENTION AND PREFERRED EMBODIMENTS

As the developers which are soluble in solvents and of which at least one hydroxyl group with a developing function is blocked by an N-substituted carbamoyl group, compounds represented by the following formulas (4) or (5) are preferable.

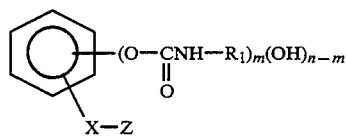

(4)

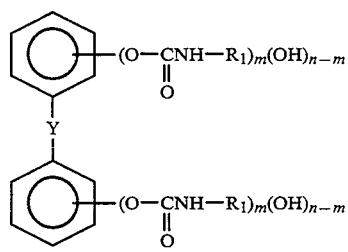

(5)

(wherein $R_1$, n and m are the same as defined in formula (1); and X, Y, and Z are the same as defined for formula (2) or (3).)

the following examples can be given of N-substituted carbamoyl groups: phenylcarbamoyl group, naphthylcarbamoyl group, cyclohexylcarbamoyl group, halogenated phenylcarbamoyl group, p-toluenesulfonylcarbamoyl group, 3,4-dichlorophenylcarbamoyl group, m-isopropenyl-α,α-dimethylbenzylcarbamoyl group, α,α-dimethylbenzylcarbamoyl group, α-methylbenzylcarbamoyl group, m-methyl-α,α-dimethylbenzylcarbamoyl group, m-ethyl-α,α-dimethylbenzylcarbamoyl group, m-propyl-α,α-dimethylbenzylcarbamoyl group, benzylcarbamoyl group, methylcarbamoyl group, ethylcarbamoyl group, n-propylcarbamoyl group, isopropylcarbamoyl group, n-butylcarbamoyl group, tert-butylcarbamoyl group, n-octadecylcarbamoyl group, chloromethylcarbamoyl group, 2-chloroethylcarbamoyl group, m-tolylcarbamoyl group, p-tolylcarbamoyl group, 2-methoxyphenylcarbamoyl group, 4-methoxyphenylcarbamoyl group, allylcarbamoyl group, and the like.

In addition, 3,3'-dichlorodiphenyl-4,4'-dicarbamoyl group, hexamethylene-1,6-dicarbamoyl group, toluene-2,4-dicarbamoyl group, and the like are given as examples of blocking groups which have two N-substituted carbamoyl groups.

Two methods are known for introducing a carbamoyl group into a phenolic hydroxy group; one involving the addition reaction of an isocyanate compound to a phenolic hydroxy group in the presence of an acid or a base, and the other comprising conversion of a phenolic compound into an aryl chloroformate compound, followed by the condensation reaction the aryl chloroformate compound with an amine compound in the presence of a base.

As a result of research directed to a process for preparing blocked developers represented by the above formula (4) or (5) in which N-substituted carbamoyl group is used as a blocking group, of the above two methods, the method using an isocyanate compound and a base was found to be preferable, and the use of benzene as a solvent was found particularly effective.

For example, in a process for the reaction of n-propyl gallate, phenylisocyanate, and triethylamine as a base, the use of a common solvent such as pyridine or ethyl acetate can proceed the reaction, but requires steps of purification of the target compound after the reaction. The use of benzene as a solvent, on the other hand, precipitates the target compound as the reaction proceeds necessitating only filtration after the reaction. This is a great advantage in an industrial process.

Illustrating the processes for preparing a blocked developer more specifically, a developer such as n-propyl gallate, n-stearyl gallate, bisphenol A, p-hydroxy benzylbenzoate, or the like and an isocyanate compound such as phenylisocyanate, cyclohexylisocyanate, octadecylisocyanate, or the like are added to benzene. A base such as pyridine, dimethylaminopyridine, or triethylamine is then added to the reaction mixture and the reaction is continued for a prescribed period of time, followed by filtration to obtain the target compound. A method of first mixing a developer and a base in benzene, and then adding an isocyanate compound to the mixture is also applicable. Dry benzene or anhydrous benzene is preferable in order to suppress the side reaction of producing urea compounds.

The reaction temperature employed may be in the range from the melting point of benzene (5° C.) to the boiling point (80° C.), with a preferable range for a faster reaction being 60–80° C. The reaction time is dependent on the time required for the precipitate to form, which is dependent on compounds reacted. Thus, the reaction time is suitably determined for each reaction. If the production of the precipitate is very slow, a concentration procedure may be necessary for the reaction solution.

A preferable amount of the isocyanate compound is in the range of 1.0–20.0 equivalent to the phenolic hydroxy group of the developer, with a preferable range being 1.0–3.0 equivalent from the aspect of suppressing the production of urea compounds from the isocyanate compound by the side reaction.

The following compounds are given as examples of carbamate-type blocked developers.

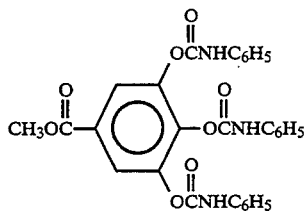

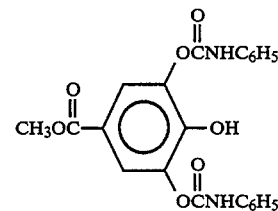

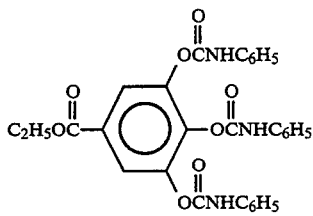

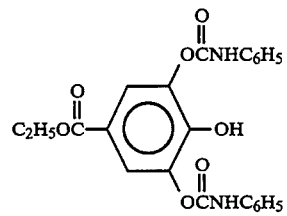

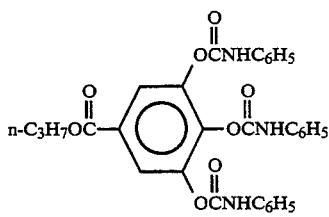

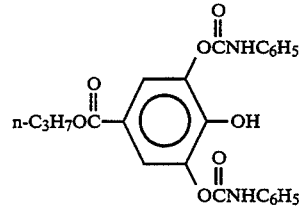

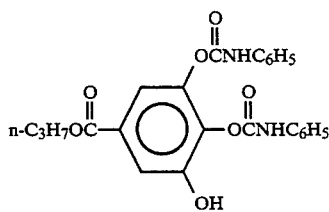

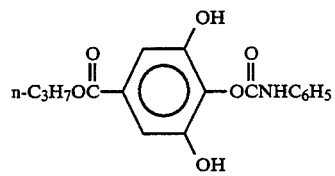

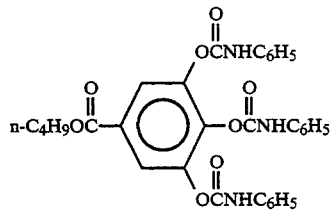

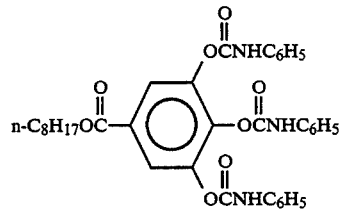

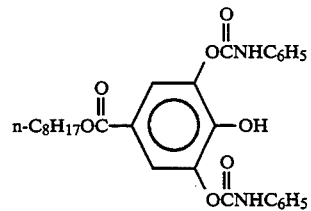

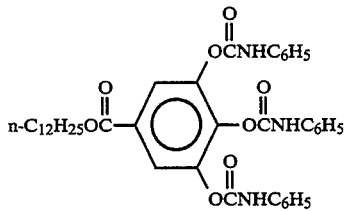

-continued
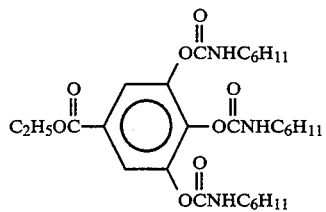
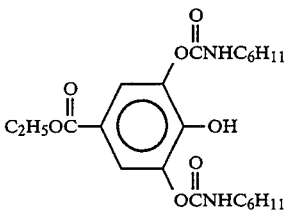
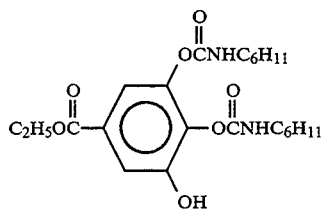
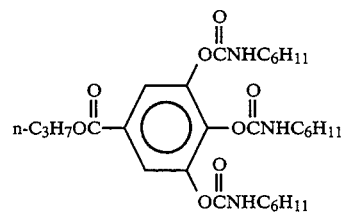
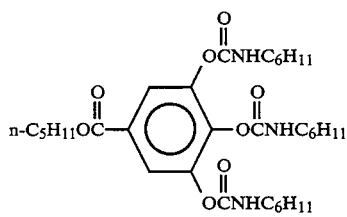
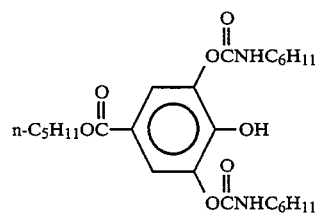
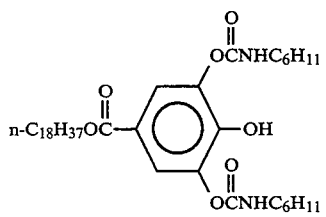
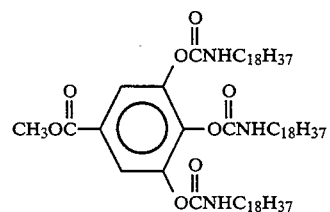
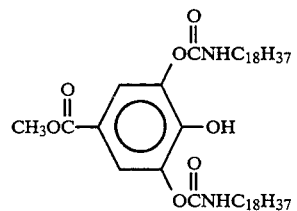
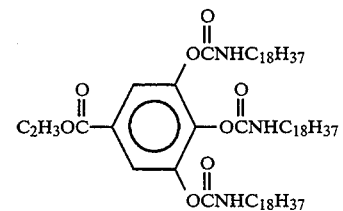
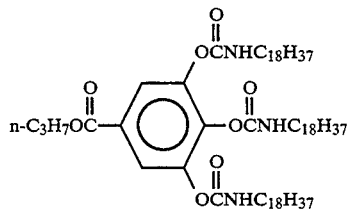
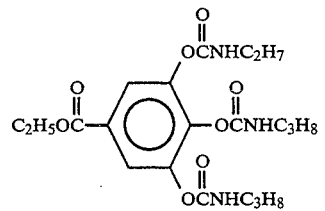
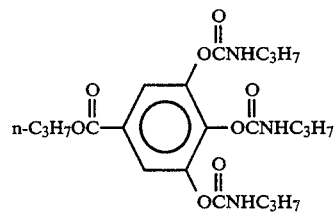
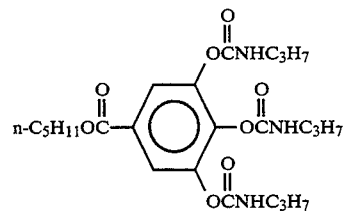

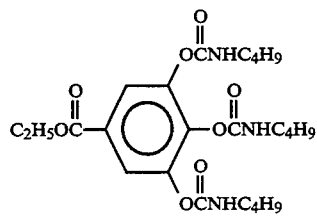
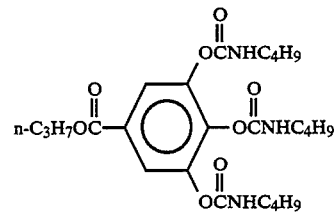
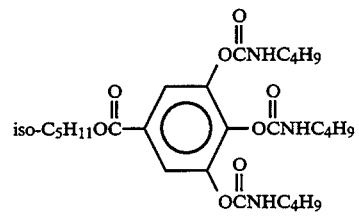
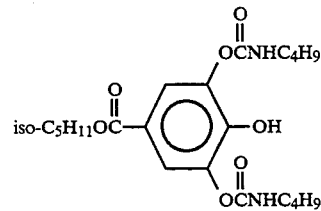
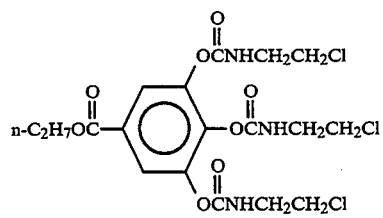
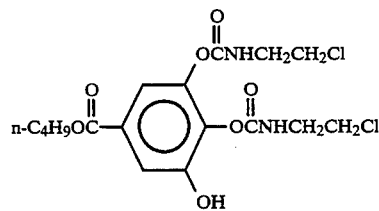
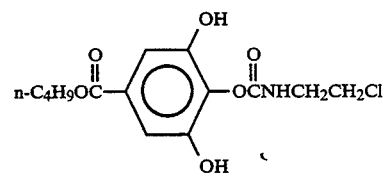
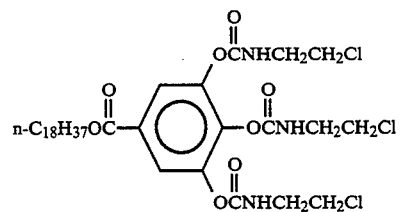
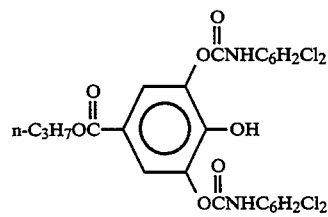
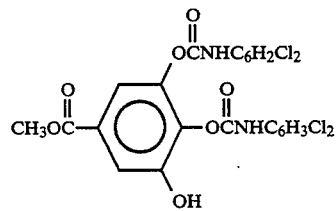
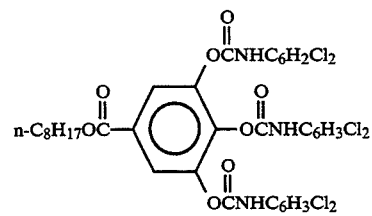
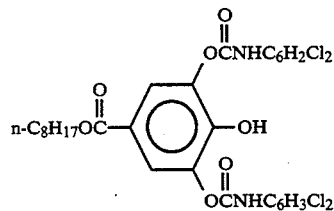
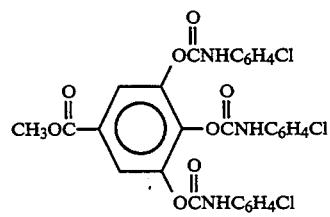
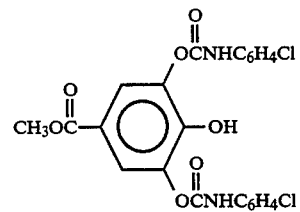

-continued
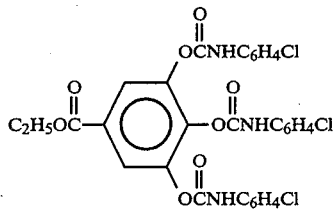
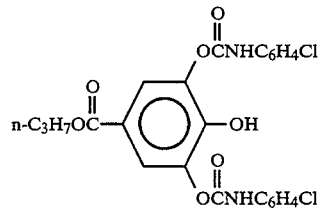
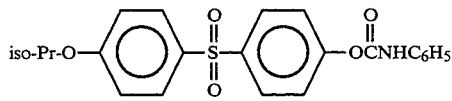
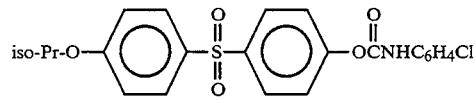
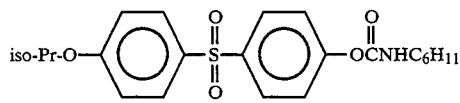
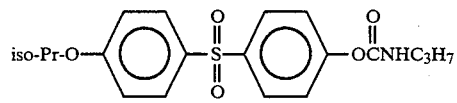
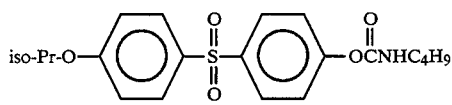
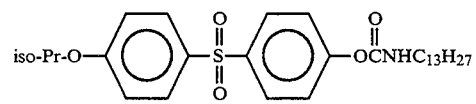
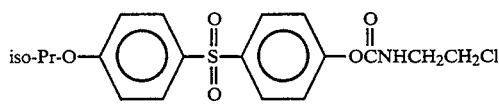
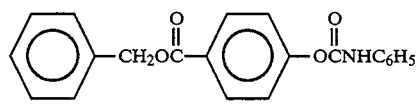
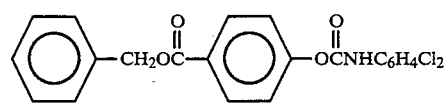
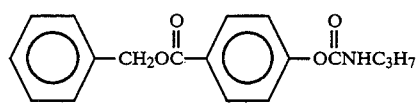
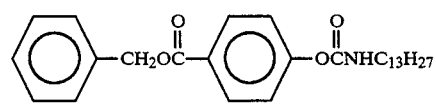
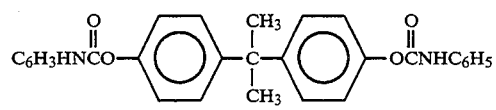
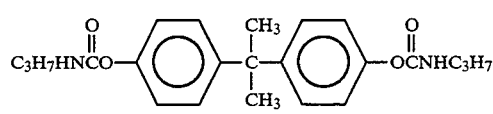
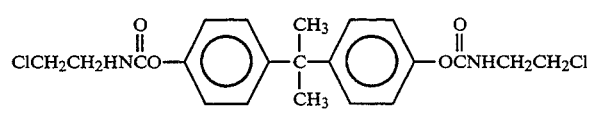
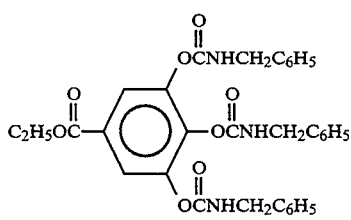
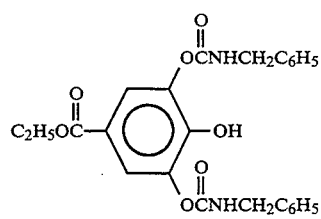
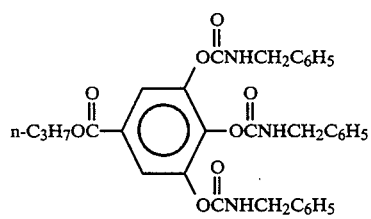
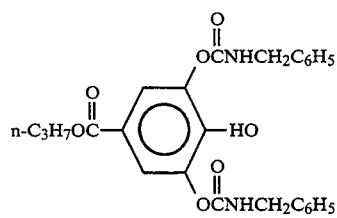

-continued
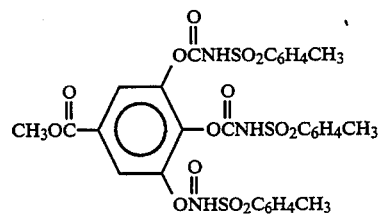
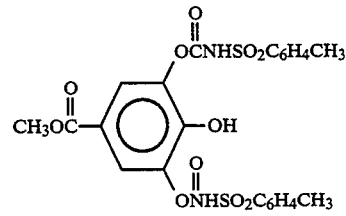
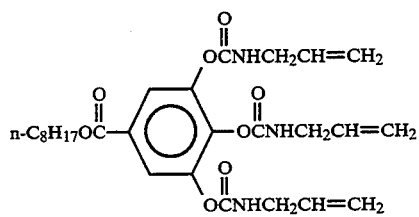
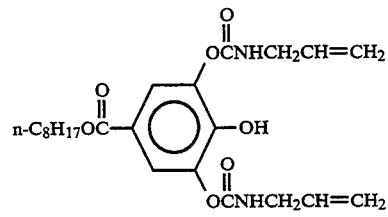
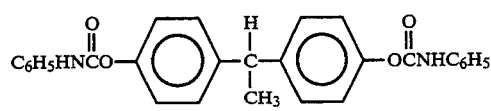
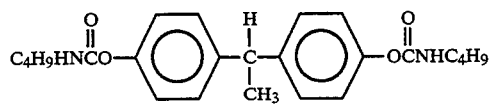
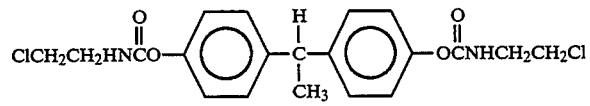
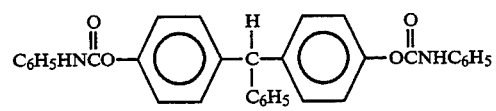
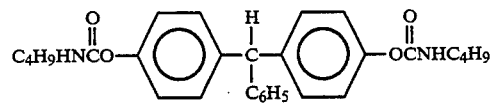
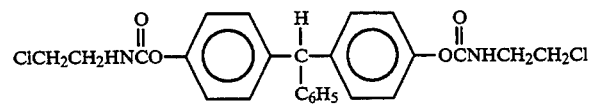
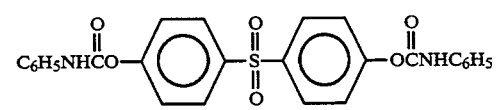
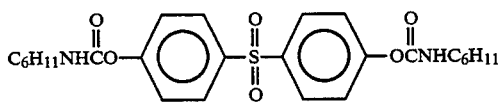
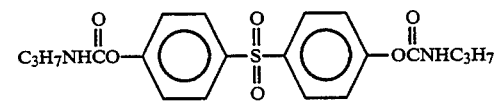
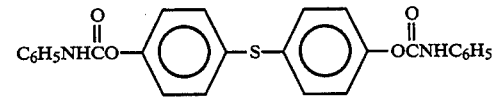
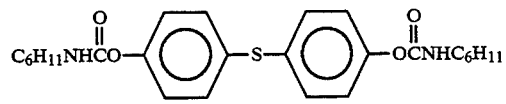
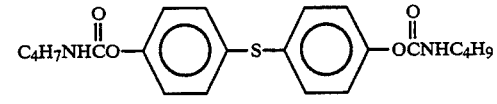
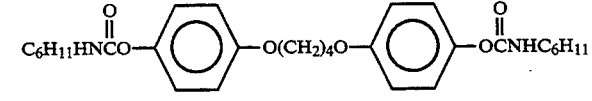
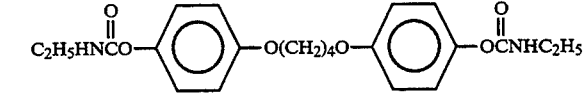
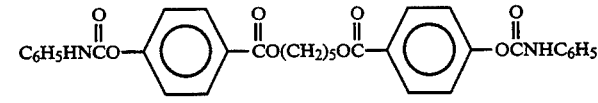

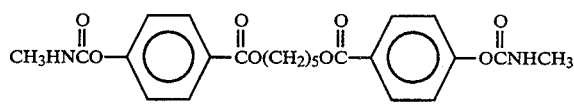
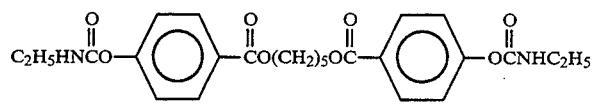
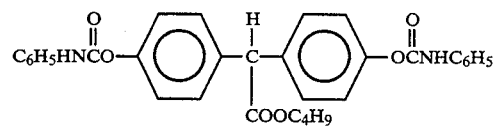
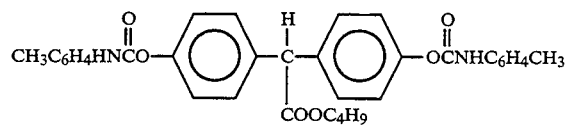
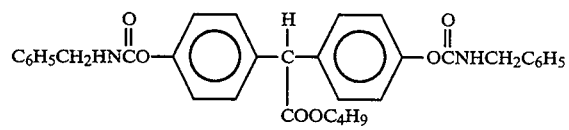
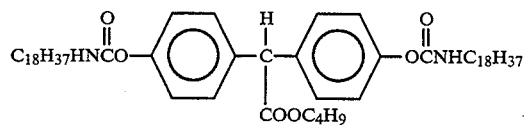
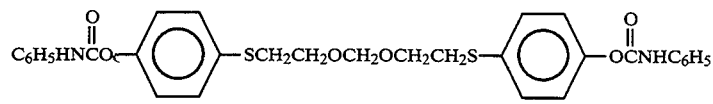
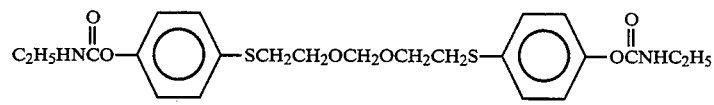
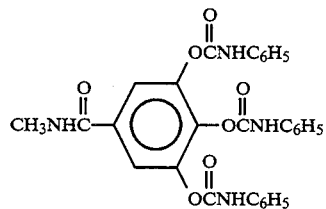
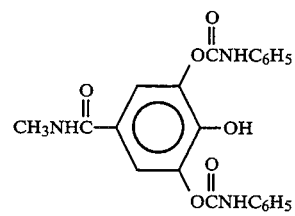
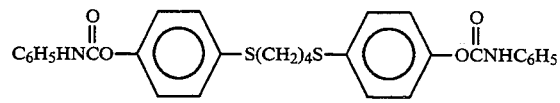
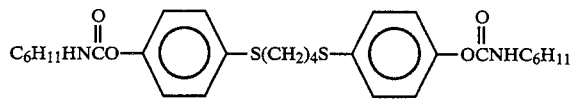
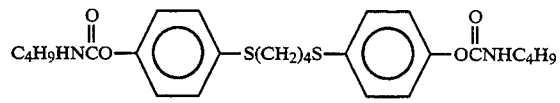
As developers which are soluble in solvents and of which at least one hydroxy group with a developing

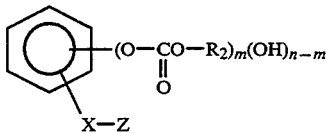
(6)

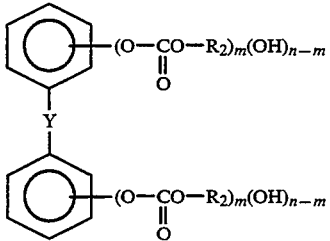
(7)

(wherein $R_2$, n and m are the same as defined in formula (1) and X, Y, and Z are the same as defined for formula (2) or (3).)

Following groups are given as examples of O-substituted oxycarbonyl groups.

—(C═O)O—$CH_3$ (methoxycarbonyl group)
—(C═O)O—$C_2H_5$ (ethoxycarbonyl group)
—(C═O)O—n—$C_3H_7$ (n-propoxycarbonyl group)
—(C═O)O—n—$C_4H_9$ (n-butoxy carbonyl group)
—(C═O)O—iso—$C_4H_9$ (iso-butoxy carbonyl group)
—(C═O)O—tert—$C_4H_9$ (tert-butoxy carbonyl group)
—(C═O)O—n—$C_{16}H_{33}$ (n-hexadecyloxycarbonyl group)
—(C═O)O—$CH_2CH$═$CH_2$ (allyloxycarbonyl group)
—(C═O)O—CH═$CH_2$ (vinyloxycarbonyl group)
—(C═O)O—$CH_2C_6H_5$ (benzyloxycarbonyl group)
—(C═O)O—$C_6H_5$ (phenyloxycarbonyl group)
—(C═O)O—$C_{10}H_7$ (naphthyloxycarbonyl group)
—(C═O)O—$CH_2CH_2CCl_3$ (2,2,2-trichloroethoxycarbonyl group)
—(C═O)O—$CH_2CH_2Si(CH_3)_3$ (2-trimethylsilyl)ethoxycarbonyl group)

As methods for introducing an O-substituted oxycarbonyl group into a phenolic hydroxy group, a method reacting an alkyl chloroformate or an aryl chloroformate and a phenolic compound in the presence of a base, a method reacting a dicarbonate compound and a phenolic compound in the presence of a base, and the like are known in the art. Blocked developers of formula (6) or (7) can be prepared by these methods.

The following compounds can be given as examples of carbonate-type blocked developers.

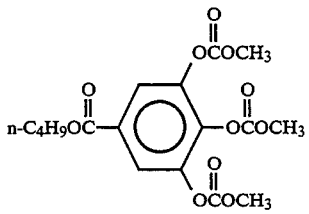
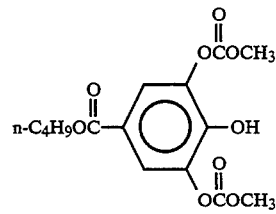
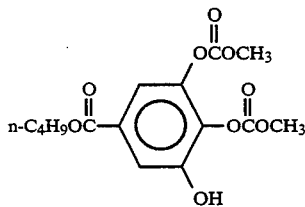
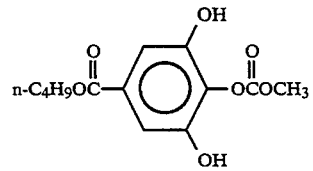
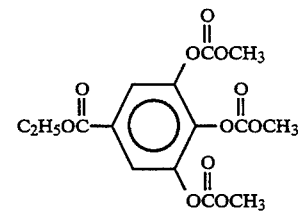
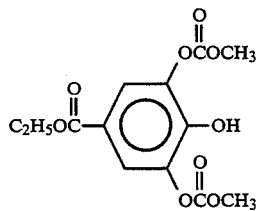
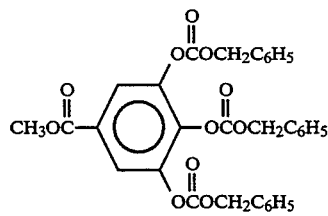
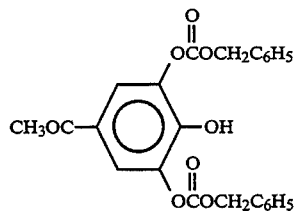

-continued
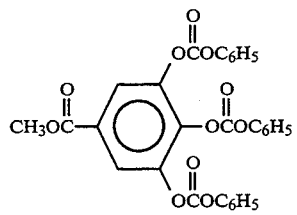
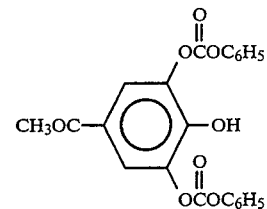
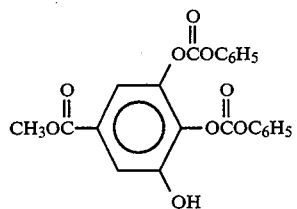
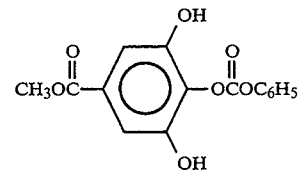
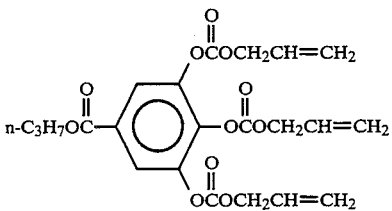
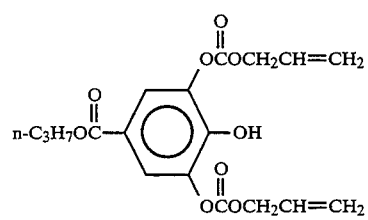
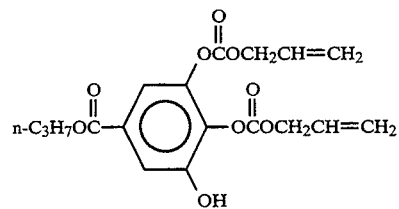
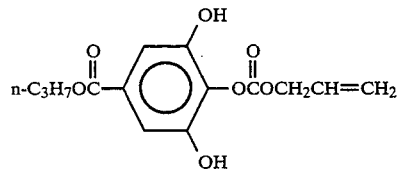
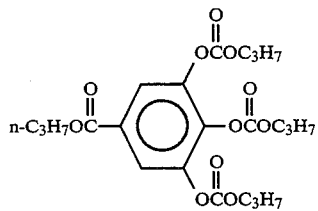
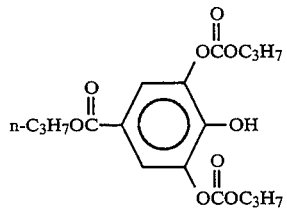
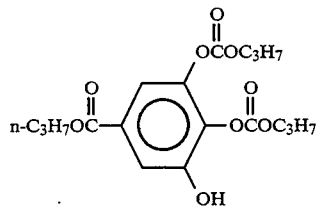
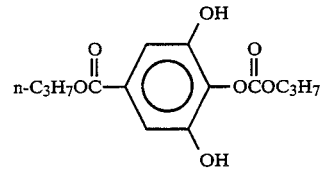
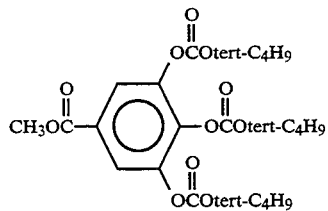
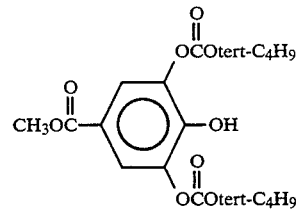

21 22
-continued
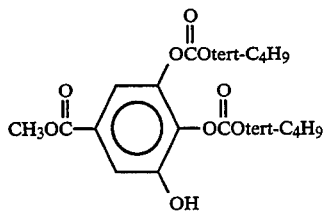
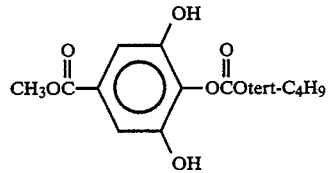
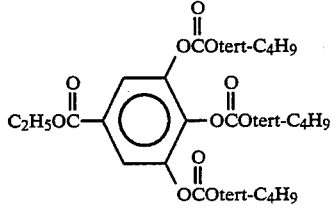
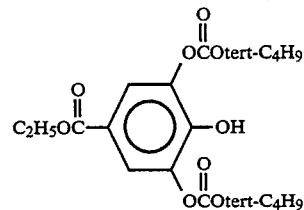
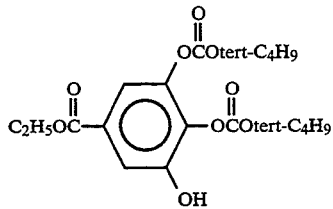
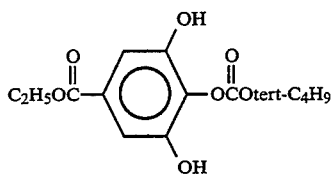
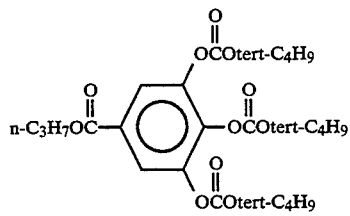
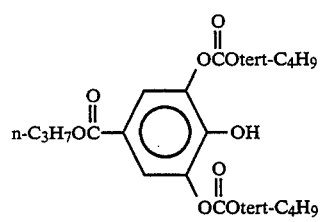
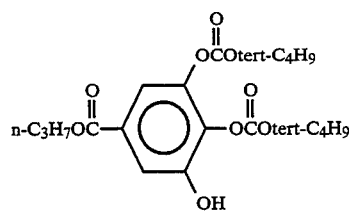
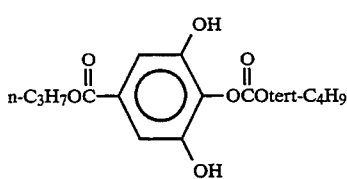
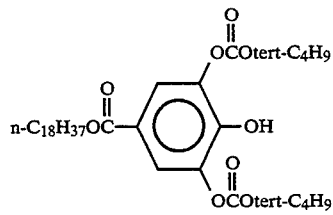
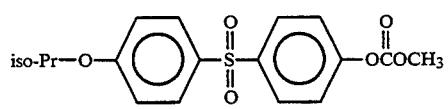
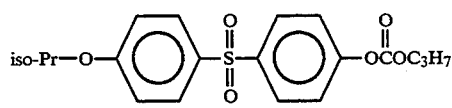
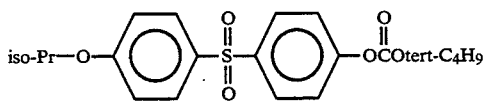
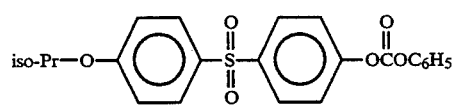
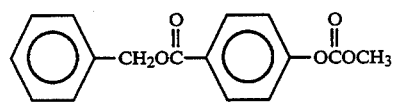
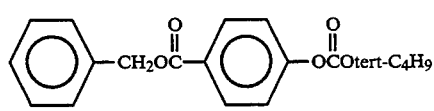
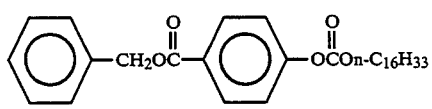

-continued
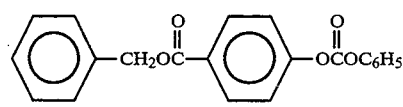
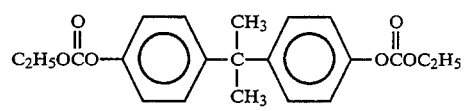
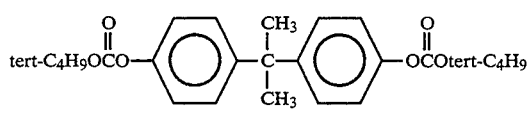
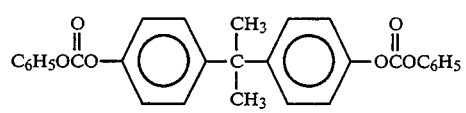
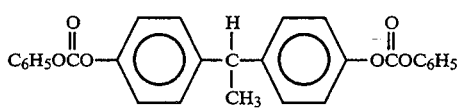
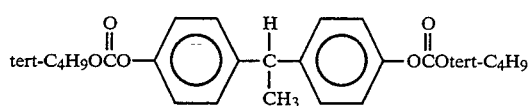
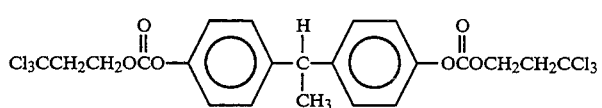
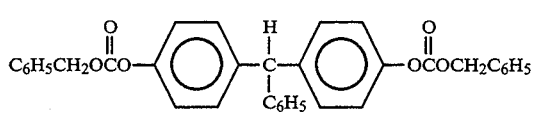
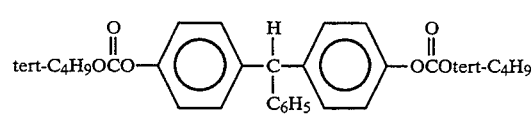
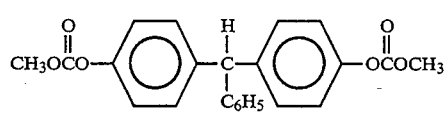
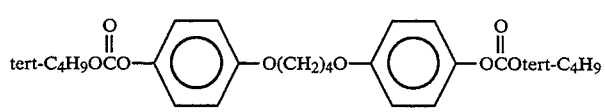
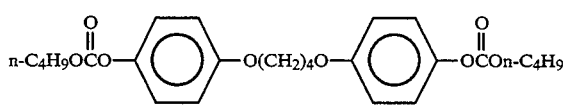
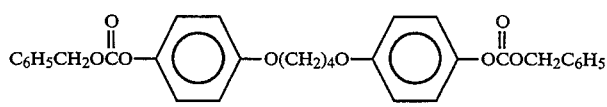
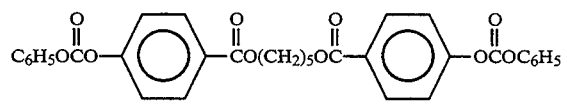
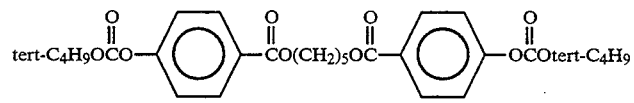
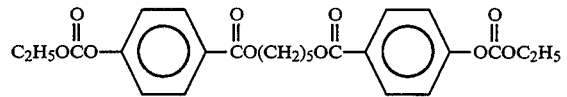
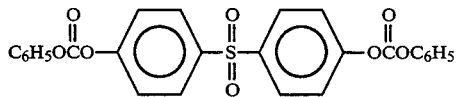
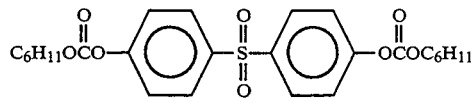

-continued

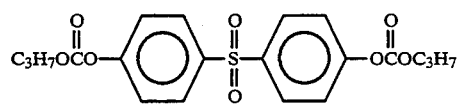
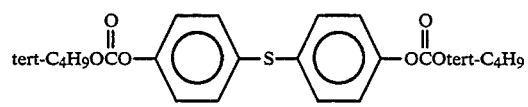
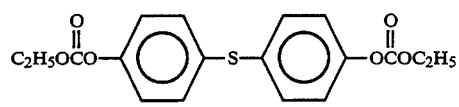
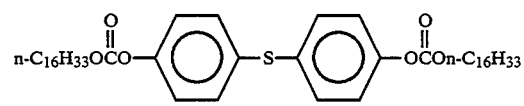
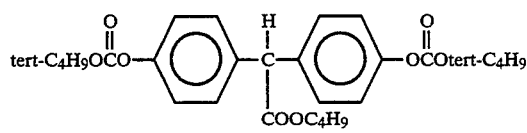
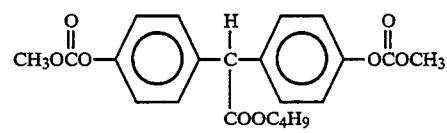
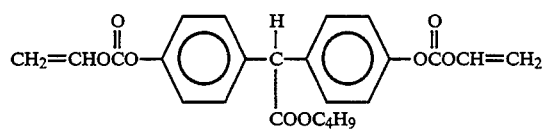
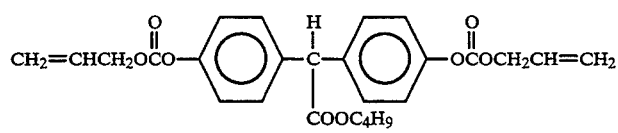
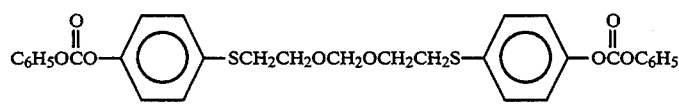
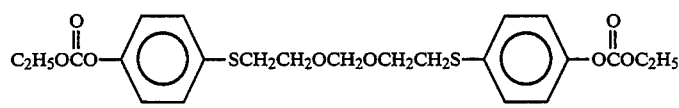
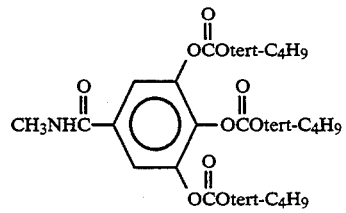
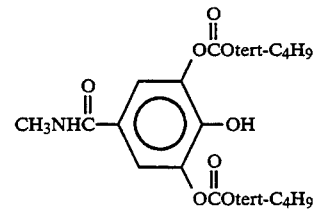
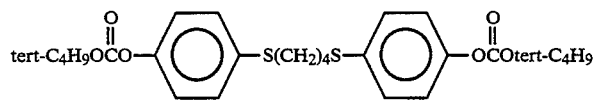
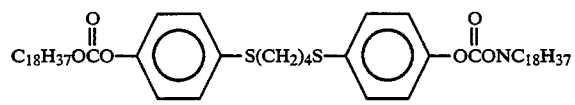
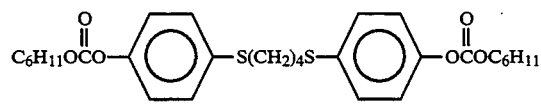

In the present invention, when 2 or more hydroxy groups with a developing function are present, an N-substituted carbonyl group and an O-substituted oxycarbonyl group may be present together in order to block the hydroxy groups.

Preferable organic acids for the metal salt used in the present invention are o- or m-substituted benzoic acids, such as o-benzoylbenzoic acid, o-alkyl substituted benzoylbenzoic acid, o-, m-alkylbenzoic acid, o-tolylbenzoic acid, m-tolylbenzoic acid, o-halogenobenzoic acid, and m-halogenobenzoic acid, and the like.

A metal in the metal salt is preferably iron, silver, vanadium, or cobalt, with iron being the most preferable.

Any colorless electron-donor dye conventionally known in the field of heat-sensitive recording paper can be used as a leuco dye in the present invention. The following compounds can be given as typical examples:
crystal violet lactone,
3-diethylamino-6-methyl-7-anilinofluorane,
3-diethylamino-benzo [C] fluorane,
3,6-di(n-dimethylamino)-fluoran-9-spiro-3-(6-dimethylamino) phthalide,
3-dibutylamino-6-methyl-7-anilinofluorane,
3-(N-ethyl-N-isoamylamino)-6-methyl-7-anilinofluorane,
4-diethylamino-2-ethoxyphenyl)-3-(1-ethyl2methylindol-3-yl)-4-azaphthalide, and
3-(N-ethyl-N-cyclohexyl-amino)6-methyl-7-anilinofluorane.

The above developers, leuco dyes and metal salts of an organic acid are dissolved in a solvent suitable for use in painting, such as toluene, methyl ethyl ketone (MEK), acetone, chloroform, or the like, together with a binder.

Conventionally, in the case where a leuco dye, which is a heat-sensitive coloring material, and a developer are used by dissolving in a solvent together with a binder, a number of binders are seen to act to reduce the sensitivity. In extreme cases, compositions may develop no color. Accordingly, there are limitations to the selection of the binder.

However, when a developer represented by formula (1), wherein at least one phenolic hydroxyl group with a developing function is blocked is used according to the present invention, this type of limitation is considerably alleviated. In particular, when the developer is combined with a metal salt of an organic acid, this concern completely disappears and there is the advantage that various types of binders can be selected.

Examples of binders which can be preferably used in the present invention include polystyrene, polyvinylbutyral, polyester, styrene-butadiene-acrylic copolymer, silicone varnish, EB, and UV-curable resin.

In the preparation of an optical recording medium, a light absorbing agent is dissolved along with the above components and becomes part of the transparent recording layer. Specific examples of light absorbing agents which are preferably used when the light source is a semiconductor laser beam include inmonium or diinmonium compounds such as IRG002 or IRG022 (trademarks, manufactured by Nippon Kayaku Co., Ltd.), dithiol nickel complexes, cyanine dyes such as 1,1,5,5-tetrakis(p-dimethylaminophenyl)-3-methoxy-1,4-pentadiene, or 1,1,5,5-tetrakis(p-dimethylaminophenyl)-3-[2,2-bis(p-dimethylaminophenyl)vinyl]-1,4-pentadiene, squalerium dyes, naphthoquinone dyes, phthalocyanine, and naphthalocyanine compounds with a light color, and the like.

Preferable support members are films, sheets, and plates of glass or synthetic resins, such as polyester resin, polycarbonate resin, poly(methyl methacrylate) resin, polystyrene, polyethylene, and the like, possessing heat resistance and high transparency.

The composition of components for producing a recording layer of the transparent recording medium according to the present invention is approximately 3-30 parts of a blocked developer, 3-30 parts of a leuco dye or a metal salt of an organic acid, 10-30 parts of a binder, and 1-10 parts of a light absorbing agent. A solution of these components in a solvent containing about 20% solids is applied to a transparent supporting medium and dried to obtain a transparent optical recording medium.

The recording medium of the present invention thus prepared is useful as a sheet for OHP and a slide film, and as a printing photomask for manufacturing resin wire distributors or integrated circuit boards, owing to its recording capability.

Recording onto the transparent recording medium can be more preferably carried out by means of laser beam than by means of a thermal head. A clear record can be obtained by using a semiconductor laser beam of approximately several tens of mW.

A transparent coating liquid with undeveloped color can be obtained by dissolving a soluble blocked developer of formula (1) and a metal salt of an organic acid or a leuco dye in an organic solvent. Since the hydroxy groups with a developing function in the developer are blocked, the coating liquid is coated onto a transparent substrate and dried without the occurrence of a color development reaction to produce an almost colorless transparent layer, even though the developer and a leuco dye are present in the proximity of a molecular level. A colored image can be obtained by heating the coated layer by a thermal head or the like to remove the blocking groups, thus making the developer function and immediately react. In the case of a transparent recording medium having a recording layer to which a solution of a near-infrared absorbing agent is added, irradiation by a laser beam can convert light energy into heat energy to efficiently release the blocking groups, resulting in production of the hydroxy groups with a developing function. Thus, a laser beam can produce a recoded image with higher density at a higher speed than a thermal head.

Other features of the invention will become apparent in the course of the following description of the exemplary embodiments which are given for illustration of the invention and are not intended to be limiting thereof.

EXAMPLES

Preparation of Blocked Developer

Synthesis Example 1

1.06 gm (5 mM) of n-propyl gallate, 2.17 ml (20 mM) of phenylisocyanate, and 20 ml of dry benzene were filled into a dry Florence flask and heated to 60° C. on an oil bath. 0.1 ml (0.7 mM) of triethylamine was then added, and the mixture was stirred for 10 minutes in an nitrogen atmosphere. A white precipitate was produced which was filtered with the addition of benzene to obtain a product in a yield of 2.40 gm. The product was recrystallized from a mixed solvent of acetone and benzene. This product was confirmed to be a blocked developer with three hydroxyl groups of gallic acid blocked by phenyl carbamoyl groups by $^1$H-NMR and by the fact that there was no color development when dissolved in a solvent (MEK) together with CVL.

$^1$H-NMR: 1.02(3H, t, J=7.0), 1.80(2H, m), 4.31(2H, t, J=7.0), 7.00–8.00(19H, m)

Synthesis Example 2

0.51 ml (4 mM) of cyclohexylisocyanate and 4 ml of dry benzene were added to 212 mg (1 mM) of n-propyl gallate. After the addition of 2 drops of triethylamine, the reaction mixture was stirred for 1 hour at 70° C., followed by filtration with the addition of benzene to obtain 455 mg of n-propyl gallate tri-N-cyclohexylcarbamate. The compound was identified in the same manner as in Example 1.

$^1$H-NMR: 1.00(3H, t, J=7.0), 1.05–1.60(17H, m), 1.70–2.10(18H, m), 4.25(2H, t, J=7.0), 5.20(3H, m), 7.78(2H, s)

Synthesis Example 3

1.06 gm (5 mM) of monopropoxydiphenolsulfone, 2.17 ml (20 mM) of phenylisocyanate, and 20 ml of dry benzene were filled into a dry Florence flask and heated to 60° C. on an oil bath. 0.1 ml (0.7 mM) of triethylamine was then added, and the mixture was stirred for 10 minutes in a nitrogen atmosphere. A white precipitate was produced which was filtered from benzene to obtain a product in a yield of 1.47 gm. The product was dissolved in a mixture of acetone and benzene and recrystallized. This product was confirmed to be a blocked developer with one hydroxy group of monopropoxydiphenylsulfone blocked by phenyl carbamoyl group by $^1$H-NMR and by the fact that there was no color development when this developer was dissolved in a solvent (MEK) together with CVL.

$^1$H-NMR: 1.30(3H, s), 1.32(3H, s), 4.75(1H, m), 7.09–8.00(14H, m)

Synthesis Example 4

1.06 gm (5 mM) of n-propyl gallate was dissolved in 20 ml of ethyl acetate. To the solution were added 5.7 ml (25 mM) of di-tert-butyldicarbonate and 2 ml of pyridine. The mixture was reacted for 10 hours at room temperature in a nitrogen atmosphere. The reaction mixture was concentrated and purified by silica gel column chromatography using an eluent of a 1:2 (v/v) mixture of ethyl acetate and n-hexane. The product was confirmed by $^1$H-NMR to be a developer with tert-butoxycarbonyl group (—C(=O)O-tert-butyl) introduced into 2 hydroxyl groups out of 3 of n-propyl gallate. $^1$H-NMR: 1.01(3H, t, J=7.0), 1.56(18H, s), 1.77(2H, m), 4.24(2H, t, J=7.0), 7.79(2H, s)

Synthesis Example 5

1.06 gm (5 mM) of n-propyl gallate was dissolved in 20 ml of ethyl acetate. To the solution were added 1.9 ml (25 mM) of methyl chlorocarbonate and 2 ml of pyridine. The mixture was reacted for 3 hours at 50° C. in a nitrogen atmosphere. The reaction mixture was diluted with ethyl acetate, washed with a saturated aqueous solution of sodium bicarbaonate and saturated brine, dried over anhydrous sodium sulfate, and concentrated. An oily product thus obtained was purified by silica gel column chromatography using an eluent of a 1:2 (v/v) mixture of ethyl acetate and n-hexane. The product was confirmed by $^1$H-NMR to be n-propyl gallate trimethylcarbonate.

$^1$H-NMR: 1.01(3H, t, J=7.4), 1.78(2H, m), 3.92(3H, s), 3.93(6H, s), 4.28(2H, t, J=7.4), 7.91(2H, s)

Synthesis Example 6

1.06 gm (5 mM) of monopropoxydiphenolsulfone was dissolved in 20 ml of ethyl acetate. To the solution were added 3.5 ml (15 mM) of di-tert-butyldicarbonate and 2 ml of pyridine. The mixture was reacted for 3 hours at 50° C. in a nitrogen atmosphere. The reaction mixture was concentrated and purified by silica gel column chromatography using an eluent of a 1:2 (v/v) mixture of ethyl acetate and n-hexane. The product was confirmed by $^1$H-NMR to be a compound with hydroxyl groups of monopropoxydiphenolsulfone blocked with tert-butoxycarbonyl group (—C(=O)O-tert-butyl).

$^1$H-NMR: 1.33(3H, s), 1.35(3H, s), 1.55(9H, s), 4.60(1H, m), 6.92(2H, dt, J=8.5, 3.0), 7.29(2H, dt, J=8.5, 3.0), 7.83(2H, dt, J=8.5, 3.0), 7.94(2H, dt, J=8.5, 3.0).

Synthesis Example 7

228 mg (1 mM) of bisphenol A was dissolved in 2 ml of ethyl acetate. To the solution were added 0.69 ml (3 mM) of di-tert-butyldicarbonate and 0.1 ml of pyridine. The mixture was reacted for 3 hours at 50° C. in a nitrogen atmosphere. The reaction mixture was concentrated and purified by silica gel column chromatography using an eluent of a 1:2 (v/v) mixture of ethyl acetate and n-hexane. The product was confirmed by $^1$H-NMR to be a compound with hydroxyl groups of bisphenol A blocked with tert-butoxycarbonyl group (—C(=O)O-tert-butyl).

$^1$H-NMR: 1.55(18H, s), 1.65(6H, s), 7.05(4H, dt, J=8.5, 2.5), 7.21(4H, dt, J=8.5, 2.5)

Preparation of Transparent Recording Medium

EXAMPLE 1

The following mixture was dissolved in a solvent (MEK) to a solid content of 20%.

| | |
|---|---|
| Blocked developer of Synthesis Example 1 | 20 parts |
| Soluble iron salt (iron o-benzoylbenzoate) | 20 parts |
| Binder (polyvinylbutyral) | 20 parts |
| Light absorbing agent (IRGO02)* | 1 part |

*Trademark, manufactured by Nihon Kayaku Co., Ltd.

The resulting coating liquid for recording was applied to a transparent polyester film using a Mayer bar in an amount of 5 gm/m$^2$, and dried in air at room temperature to obtain a transparent recording sheet.

When this transparent recording medium was scanned at 40 mm/sec using a semiconductor laser beam with a 30 mW output, black recorded lines of a 50 μm line width were obtained.

A heat resistance test at 60° C. revealed absolutely no color change.

When this recording film was mounted on a slide and projected, the black lines were magnified clearly. Also, the recorded film projected over an OHP produced enlarged clear black lines.

EXAMPLE 2

A transparent recording sheet was obtained in exactly the same manner as in Example 1, except that 0.2 parts of 1,1,5,5-tetrakis(p-dimethylaminophenyl)-3-methoxy-1,4-pentadiene was substituted for the light absorbing agent in Example 1. When this transparent recording medium was scanned at 40 mm/sec using a semiconductor laser beam with a 30 mW output, black recorded lines of a 50 μm line width were obtained.

EXAMPLE 3

A transparent recording sheet was obtained in exactly the same manner as in Example 1, except that 10 parts of toluenedithiol nickel complex was substituted for the light absorbing agent of Example 1. When this transparent recording medium was scanned at 40 mm/sec using a semiconductor laser beam with a 30 mW output, black recorded lines of a 45 μm line width were obtained.

EXAMPLE 4

A recording coating liquid was obtained in the same manner as in Example 1, except that 20 parts of an ultraviolet-curable resin GRANDIC UV5020 (trademark, manufactured by Dainippon Ink & Chemicals Inc.) was substituted for the binder of Example 1. The resulting recording coating liquid in an amount of 5 gm/m$^2$ was applied to a transparent polyester film using a Mayer bar, after which a transparent recording sheet was obtained by curing the UV-curable resin with an ultraviolet light irradiated from a UV emitting device (one lamp, output 3 KW, manufactured by the Eyegraphic Co.) at a distance of 12 cm from the surface of the coated layer, while the film was moved at a speed of 5/min.

When this transparent recording medium was scanned at 40 mm/sec using a semiconductor laser beam with a 30 mW output, recorded lines of a 50 μm line width were obtained.

EXAMPLE 5

The following mixture was dissolved in a solvent (toluene) to a solid content of 20%.

| | |
|---|---|
| Blocked developer of Synthesis Example 1 | 5 parts |
| Soluble iron salt (iron o-benzoylbenzoate) | 5 parts |
| Binder (polystyrene) | 20 parts |
| Light absorbing agent (IRG002)* | 1 part |

*Trademark, manufactured by Nihon Kayaku Co., Ltd.

The resulting coating liquid for recording was applied to a transparent polyester film using a Mayer bar in an amount of 5 gm/m$^2$, and dried in air at room temperature to obtain a transparent recording sheet.

When this transparent recording medium was scanned at 40 mm/sec using a semiconductor laser beam with a 30 mW output, black recorded lines of a 45 μm line width were obtained.

EXAMPLE 6

The following mixture was dissolved in a solvent (MEK) to a solid content of 20%.

| | |
|---|---|
| Blocked developer of Synthesis Example 1 | 20 parts |
| Soluble iron salt (iron o-chlorobenzoate) | 20 parts |
| Binder (polyvinylbutyral) | 20 parts |
| Light absorbing agent (NK-2014)* | 1 part |

*Trademark, manufactured by Japan Photosensitive Dye Laboratory

The resulting coating liquid for recording was applied to a transparent polyester film using a Mayer bar in an amount of 5 gm/m$^2$, and dried in air at room temperature to obtain a transparent recording sheet.

When this transparent recording medium was scanned at 40 mm/sec using a semiconductor laser beam with a 30 mW output, black recorded lines of a 50 μm line width were obtained.

EXAMPLE 7

A transparent recording sheet was obtained in exactly the same manner as in Example 6, except that as a soluble iron salt 20 parts of iron o-benzoylbenzoate was used instead of iron o-chlorobenzoate of Example 6. When this transparent recording medium was scanned at 40 mm/sec using a semiconductor laser beam with a 30 mW output, black recorded lines of a 50 μm line width were obtained.

EXAMPLE 8

The following mixture was dissolved in a solvent (MEK) to a solid content of 20%.

| | |
|---|---|
| Blocked developer of Synthesis Example 2 | 15 parts |
| Soluble iron salt (iron o-benzoylbenzoate) | 25 parts |
| Binder (polyvinylbutyral) | 20 parts |
| Light absorbing agent (1,1,5,5-tetrakis(p-dimethylaminophenyl)-3-methoxy-1,4-pentadiene) | 0.2 part |

The resulting coating liquid for recording was applied to a transparent polyester film using a Mayer bar in an amount of 5 gm/m$^2$, and dried in air at room temperature to obtain a transparent recording sheet.

When this transparent recording medium was scanned at 40 mm/sec using a semiconductor laser beam with a 30 mW output, black recorded lines of a 50 μm line width were obtained.

EXAMPLE 9

The following mixture was dissolved in a solvent (chloroform) to a solid content of 10%.

| | |
|---|---|
| Blocked developer of Synthesis Example 2 | 8 parts |
| Soluble iron salt (iron o-benzoylbenzoate) | 12 parts |
| Binder (polyvinylbutyral) | 20 parts |
| Light absorbing agent (IRG002) | 1 part |

*Trademark, manufactured by Nihon Kayaku Co., Ltd.

The resulting coating liquid for recording was applied to a transparent polyester film using a Mayer bar in an amount of 5 gm/m$^2$, and dried in air at room temperature to obtain a transparent recording sheet.

When this transparent recording medium was scanned at 40 mm/sec using a semiconductor laser beam with a 30 mW output, black recorded lines of a 50 μm line width were obtained.

A heat resistance test at 60° C. revealed absolutely no color change.

The recording film was mounted on a slide and projected to obtain clear magnification of the blue lines.

EXAMPLE 10

The following mixture was dissolved in a solvent (a 1:1 (v/v) mixture of chloroform and acetone) to a solid content of 20%.

| | |
|---|---|
| Blocked developer of Synthesis Example 3 | 20 parts |
| Leuco dye (crystal violet lactone) | 20 parts |
| Binder (polystyrene) | 20 parts |

| Light absorbing agent (toluenedithiol nickel complex) | 10 parts |

The resulting coating liquid for recording was applied to a transparent polyester film using a Mayer bar in an amount of 5 gm/m², and dried in air at room temperature to obtain a transparent recording sheet.

When this transparent recording medium was scanned at 40 mm/sec using a semiconductor laser beam with a 30 mW output, black recorded lines of a 40 μm line width were obtained.

A heat resistance test at 60° C. revealed absolutely no color change.

The recording film was mounted on a slide and projected to obtain clear magnification of the blue lines.

EXAMPLE 11

A transparent recording sheet was obtained in exactly the same manner as in Example 10, except that 20 parts of bis(dithiobenzyl) nickel complex was used instead of the light absorbing agent of Example 10. When this transparent recording medium was scanned at 40 mm/sec using a semiconductor laser beam with a 30 mW output, blue recorded lines of a 45 μm line width were obtained.

EXAMPLE 12

A transparent recording sheet was obtained in the same manner as in Example 1, except that the blocked developer of Synthesis Example 4 was used. When this transparent recording medium was scanned at 40 mm/sec using a semiconductor laser beam with a 30 mW output, black recorded lines of a 50 μm line width were obtained.

A heat resistance test at 60° C. revealed absolutely no color change.

The recording film was mounted on a slide and projected to obtain clear magnification of the black lines. Also, the recorded film projected over an OHP produced enlarged clear black lines.

EXAMPLE 13

A transparent recording sheet was obtained in the same manner as in Example 6, except that the blocked developer of Synthesis Example 4 was used. When this transparent recording medium was scanned at 40 mm/sec using a semiconductor laser beam with a 30 mW output, black recorded lines of a 50 μm line width were obtained.

EXAMPLE 14

The following mixture was dissolved in a solvent (MEK) to a solid content of 20%.

| Blocked developer of Synthesis Example 5 | 20 parts |
| Soluble iron salt (iron o-chlorobenzoate) | 20 parts |
| Binder (polyvinylbutyral) | 20 parts |
| Light absorbing agent (1,1,5,5-tetrakis(p-dimethyl-aminophenyl)-3-methoxy-1,4-pentadiene) | 0.3 part |

The resulting coating liquid for recording was applied to a transparent polyester film using a Mayer bar in an amount of 5 gm/m², and dried in air at room temperature to obtain a transparent recording sheet.

When this transparent recording medium was scanned at 40 mm/sec using a semiconductor laser beam with a 30 mW output, black recorded lines of a 50 μm line width were obtained.

EXAMPLE 15

A transparent recording sheet was obtained in the same manner as in Example 1, except that the blocked developer of Synthesis Example 5 was used. When this transparent recording medium was scanned at 40 mm/sec using a semiconductor laser beam with a 30 mW output, black recorded lines of a 50 μm line width were obtained.

EXAMPLE 16

A transparent recording sheet was obtained in the same manner as in Example 10, except that the blocked developer of Synthesis Example 6 was used. When this transparent recording medium was scanned at 40 mm/sec using a semiconductor laser beam with a 30 mW output, blue recorded lines of a 40 μm line width were obtained.

EXAMPLE 17

A transparent recording sheet was obtained in the same manner as in Example 11, except that the blocked developer of Synthesis Example 7 was used. When this transparent recording medium was scanned at 40 mm/sec using a semiconductor laser beam with a 30 mW output, blue recorded lines of a 45 μm line width were obtained.

As illustrated in the foregoing description, the use of a blocked developer according to the present invention, which does not develop a color when mixed and dissolved with a coloring agent, ensures efficient production of a transparent optical recording medium by means of painting of one coating layer. The transparent recording medium of the present invention can directly record minute images without contact by radiation such as laser beam, thus it can significantly shorten the time required for the recording.

If used as an output sheet for a printer, the transparent recording medium can immediately produce sheets for use in OHP or printed sheets for copying.

Obviously, numerous modifications and variations of the present invention are possible in light of the above teachings. It is therefore to be understood that within the scope of the appended claims, the invention may be practiced otherwise than as specifically described herein.

What is claimed is:

1. A transparent recording medium comprising a transparent supporting medium and a transparent recording layer formed on said transparent supporting medium, wherein said transparent recording layer comprises:

a developer formed by blocking at least one hydroxyl group with a developing function by an O-substituted oxycarbonyl group, —C(=O)—O—R$_2$, which developer is represented by the following formula (1), $$R\text{---}(OR_A)_m(OH)_{n-m} \tag{1}$$

wherein R is a substituted or unsubstituted aryl group, R$_A$ is the group

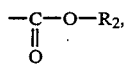

wherein $R_2$ represents a substituted or unsubstituted alkyl group, cycloalkyl group, vinyl group, allyl group, aryl group, benzyl group, naphthyl group, mesyl group, or tosyl group, $R_2$ may be the same or different when n is at least 2; n and m are integers of 1–3, provided that $m \leq n$.

2. A transparent recording medium according to claim 1, wherein said developer comprises at least one compound of the formula (2) or (3),

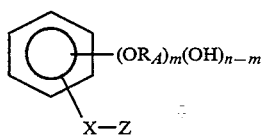

(2)

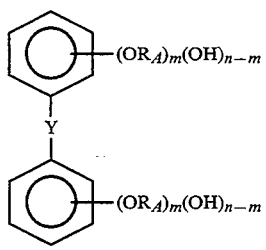

(3)

wherein $R_A$, n and m have the same meanings as in claim 1; X represents COO, CONH, or $SO_2$; Z is an alkyl group, an alkoxyphenyl group, or a benzyl group; and Y is $C(CH_3)_2$, $CHR_B$, $CH((C=O)OR_B)$, S, $SO_2$, S—$R_C$—S, O—$R_C$—O, $(C=O)(O—R_C—O(C=O))$, or S—$R_C$—O—$R_C$—O—$R_C$—S, wherein $R_B$ is an alkyl group or an aryl group; and $R_C$ is an alkylene group.

3. A transparent recording medium according to claim 2 wherein said developer is a compound represented by the formula:

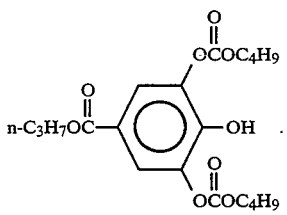

4. A transparent recording medium according to claim 2 wherein said developer is a compound represented by the formula:

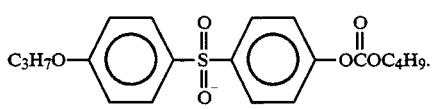

5. A transparent recording medium according to claim 2 wherein said developer is a compound represented by the formula:

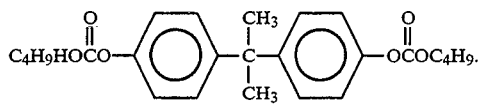

6. A transparent recording medium according to claim 2 wherein said developer is a compound represented by the formula:

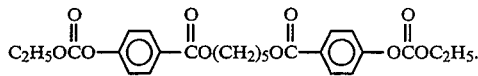

7. A transparent recording medium as claimed in claim 1, wherein said transparent recording layer comprises a light absorbing agent which absorbs light and converts the light to heat.

8. A transparent recording medium as claimed in claim 7, wherein said transparent recording layer comprises a resin which is curable by ultraviolet radiation or by an electron beam.

9. A transparent recording medium according to claim 1 wherein said developer is a compound represented by the following formula

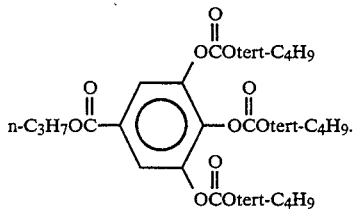

10. A transparent recording medium according to claim 1 wherein said developer is a compound represented by the following formula:

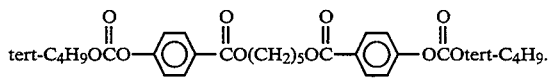

11. A transparent recording medium comprising a transparent supporting medium and a transparent recording layer formed on said transparent supporting medium, wherein said transparent recording layer comprises a developer which is a compound represented by the formula;

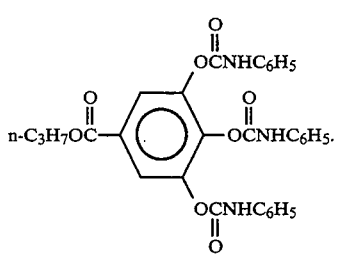

12. A transparent recording medium as claimed in claim 11, wherein said transparent recording layer comprises a light absorbing agent which absorbs light and converts the light to heat.

13. A transparent recording medium comprising a transparent supporting medium and a transparent recording layer formed on said transparent supporting medium, wherein said transparent recording layer comprises a developer which is a compound represented by the formula;

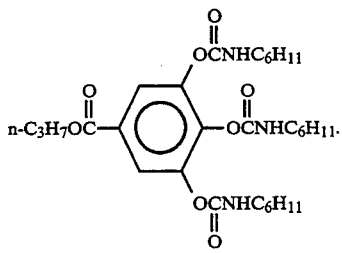

14. A transparent recording medium as claimed in claim 13, wherein said transparent recording layer comprises a light absorbing agent which absorbs light and converts the light to heat.

15. A transparent recording medium comprising a transparent supporting medium and a transparent recording layer formed on said transparent supporting medium, wherein said transparent recording layer comprises a developer which is a compound represented by the formula;

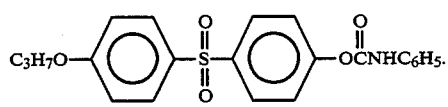

16. A transparent recording medium as claimed in claim 15, wherein said transparent recording layer comprises a light absorbing agent which absorbs light and converts the light to heat.

17. A transparent recording medium comprising a transparent supporting medium and a transparent recording layer formed on said transparent supporting medium, wherein said transparent recording layer comprises a developer which is a compound represented by the formula;

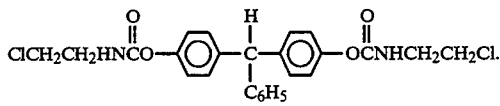

18. A transparent recording medium as claimed in claim 17, wherein said transparent recording layer comprises a light absorbing agent which absorbs light and converts light to heat.

19. A transparent recording medium comprising a transparent supporting medium and a transparent recording layer formed on said transparent supporting medium, wherein said transparent recording layer comprises a developer which is a compound represented by the formula;

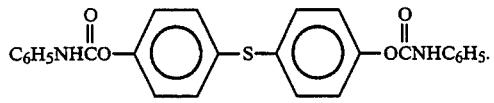

20. A transparent recording medium as claimed in claim 19, wherein said transparent recording layer comprises a light absorbing agent which absorbs light and converts the light to heat.

* * * * *